United States Patent [19]

Prescher et al.

[11] 4,088,679

[45] May 9, 1978

[54] PROCESS FOR THE PREPARATION OF PERPROPIONIC ACID SOLUTIONS

[75] Inventors: Günter Prescher, Hanau; Otto Weiberg, Neu-Isenburg; Helmut Waldmann, Leverkusen; Hermann Seifert, Cologne, all of Germany

[73] Assignees: Deutsche Gold- und Silber-Scheideanstalt vormals Roessler, Frankfurt am Main; Bayer Aktiengesellschaft, Leverkusen, both of Germany

[21] Appl. No.: 678,820

[22] Filed: Apr. 28, 1976

[30] Foreign Application Priority Data

Apr. 30, 1975 Germany ............................ 2519300

[51] Int. Cl.² .......................................... C07C 179/10
[52] U.S. Cl. .............................................. 260/502 R
[58] Field of Search ........................ 260/502 R, 502 A

[56] References Cited

FOREIGN PATENT DOCUMENTS 735,489   5/1966   Canada ........................... 260/502 R
744,391   10/1966  Canada ........................... 260/502 R

*Primary Examiner*—Bernard Helfin
*Assistant Examiner*—Werren B. Lone
*Attorney, Agent, or Firm*—Burgess, Dinklage & Sprung

[57] ABSTRACT

In the production of perpropionic acid by reaction of hydrogen peroxide and propionic acid in an aqueous medium and in the presence of an acid catalyst, e.g. sulfuric acid, to produce the peracid and water, the danger of explosion is reduced by employing a molar ratio of hydrogen peroxide to propionic acid of more than 3.5:1, a temperature of up to 60° C, and an initial hydrogen peroxide:water ratio of up to 0.8, and a catalyst concentration of 10–40% by weight.

7 Claims, No Drawings

PROCESS FOR THE PREPARATION OF PERPROPIONIC ACID SOLUTIONS

The following applications are related to the process hereof for production of propylene oxide as being directed to aspects of the process, some of which are disclosed herein.

| German Serial No. | U.S. Atty's Docket No. | U.S. Serial No. |
|---|---|---|
| P 25 19 288.5 | Bayer 2883 | 678819 |
| P 25 19 299.8 | Bayer 2885 | 678821 |
| P 25 19 298.7-42 | Bayer 2886 | 678822 |
| P 25 19 297.6 | Bayer 2887 | 678823 |
| P 25 19 295.4 | Bayer 2888 | 678824 |
| P 25 19 293.2-42 | Bayer 2889 | 678825 |
| P 25 19 292.1-42 | Bayer 2890 | 678826 |
| P 25 19 291.0-42 | Bayer 2891 | 678827 |
| P 25 19 289.6 | Bayer 2893 | 678828 |
| P 25 19 297.4 | Bayer 2893 | 678829 |

All of the German applications were filed Apr. 30, 1975. Those applications are incorporated herein by reference.

The present invention relates to a process for the preparation of perpropionic acid from hydrogen peroxide and propionic acid.

The synthesis of perpropionic acid from hydrogen peroxide and propionic acid is known (Swern, Organic Feroxides I, Wiley, 1970, page 369–372). The reaction of hydrogen peroxide with propionic acid takes place in the presence of an acid catalyst according to equation (1)

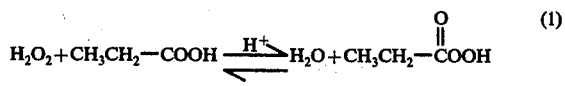

$$H_2O_2 + CH_3CH_2\text{—}COOH \underset{\rightleftarrows}{\overset{H^+}{\longrightarrow}} H_2O + CH_3CH_2\text{—}\overset{O}{\overset{\|}{C}}OOH \quad (1)$$

to give an equilibrium mixture which contains perpropionic acid, propionic acid, hydrogen peroxide, water and the acid catalyst. The concentration of perpropionic acid depends on the concentrations of the feed materials and on the molar ratio of hydrogen peroxide and propionic acid in the feed. In general, hydrogen peroxide is used in concentrations of from 30 to 90% by weight, preferably 50 to 70% by weight. Propionic acid is preferably employed in the pure form or as an aqueous solution.

Suitable acid catalysts are the mineral acids, for example sulphuric acid, acid salts, such as, for example, sodium bisulphate, or cation exchangers based on sulphonated, partially crosslinked polystyrenes in the H+ ion form. The amount of these catalysts can vary within wide limits.

The mixtures formed according to equation (1) can be used in a known manner for oxidation reactions.

The equilibrium mixtures formed according to equation (1) also arise as intermediates in processes for the preparation of anhydrous perpropionic acid solutions (DT-OS (German Published Specification) No. 2,262,970).

It is therefore extremely important to be able to prepare and handle the said reaction mixtures under explosion-proof conditions.

THE INVENTION

It is known that aqueous hydrogen peroxide, especially in a concentrated form, can form, with organic substances, mixtures which are capable of explosion and which present an explosion hazard. The explosibility of the lower percarboxylic acids in bulk and in their solutions is also known. Surprisingly, however, it was shown that reaction mixtures such as are formed by the reaction of hydrogen peroxide with propionic acid in the presence of sulphuric acid according to equation (1), present an explosion hazard even when 50% strength by weight hydrogen peroxide, that is to say a ratio by weight of hydrogen peroxide:water = 1, and anhydrous propionic acid are used.

It has now been found, surprisingly, that perpropionic acid can be prepared by reaction of hydrogen peroxide with propionic acid in the presence of an acid, preferably sulphuric acid, under explosion-proof conditions when the reaction is carried out using a molar ratio of hydrogen peroxide:propionic acid employed of more than 3.5:1, the reaction temperature is restricted to a maximum of 60° C and the ratio of hydrogen peroxide (100% by weight):water by weight before the start of the reaction with propionic acid is restricted to a maximum of about 0.8, the sulphuric acid concentration in the reaction mixture being 10–40% by weight.

Contrary to all expectations it has been found, when the reaction mixtures, under conditions of partial, well-defined enclosure in steel bombs, are exposed to heat and when the reaction mixtures are subjected to the detonation shock of a primer charge whilst enclosed in a steel tube (Explosive-stoffe 9, 4 (1961)), that reaction mixtures such as are formed according to equation (1) are explosion-proof when the molar ratio of hydrogen peroxide:propionic acid employed is restricted to more than 3.5:1, preferably 3.8–10:1, the reaction temperature is restricted to a maximum of 60° C and the ratio of hydrogen peroxide (100% by weight): water by weight before the start of the reaction with propionic acid is restricted to a maximum of about 0.8. Where sulphuric acid is used as catalyst, its concentration in the reaction mixture is preferably 10–40% by weight.

The reaction temperature in the preparation of the reaction mixtures is generally between 20° and 60° C, preferably 30°–45° C and preferentially 35°–40° C.

The present invention is illustrated by the tests which follow and the term explosion hazard, which is used there, is also explained.

EXAMPLE

There are various methods for assessing the explosion hazard of materials. For the present invention, the behaviour when exposed to heat under conditions of partial, well defined enclosure was used to assess the explosion hazard of the reaction mixtures which are formed by the reaction of hydrogen peroxide with propionic acid in the presence of sulphuric acid.

A method for determining the sensitivity of explosive materials towards exposure to heat, which leads to differentiated, comparable numerical values, is to heat the materials in a steel bomb which is closed off by a nozzle plate with a well-defined orifice. The steel bomb is fabricated from deep-drawing sheet metal and has an internal diameter of 24 mm, a length of 75 mm and a well thickness of 0.5 mm. At its open end, the bomb is provided with a collar. The bomb is closed by a circular nozzle plate provided with a bore. Nozzle plates having the following diameters for the cylindrical outlet orifice for the gases produced by the decomposition are used: 1; 1.5; 2; 2.5; 3; 3.5; 4; 4.5; 6; 8; 10; 12; 14; 16 and 20 mm.

The materials to be investigated are introduced into the steel bomb and, in order to prevent the initiation of a catalytic decomposition, the walls of the steel bomb can be provided with a coating of polyethylene or the like. The volume of the material sample is about 27 ml. The samples are exposed to heat by supplying heat in an amount of, on average, 2.4 koals/sec. from 4 Teclu burners. With 3 tests, at least one explosion must take place, the bomb being split into 3 or more parts ("limiting diameter"). The limiting diameter determined in this way is to be regarded as a measure of the heat sensitivity of the material examined. The higher the limiting diameter, the higher is the heat sensitivity. Values of 2–2.5 mm are to be regarded as transition values into the dangerous range, values in excess of 2.5 mm indicating that the reaction mixture is dangerously heat sensitive.

The reaction mixtures investigated were prepared from hydrogen peroxide of the indicated concentration using anhydrous propionic acid and concentrated sulphuric acid. The results of the steel bomb tests are given in the table which follows.

As can be seen from the table the range in which there is an explosion hazard is already reached when the ratio by weight of hydrogen peroxide:water in the hydrogen peroxide charged is increased from 0.82 to 1.0.

| Ex. No. | Ratio by weight of hydrogen peroxide:water in the hydrogen peroxide charged | Molar ratio of hydrogen peroxide: propionic acid employed | Proportion of sulphuric acid % | Limiting diameter (mm) |
|---|---|---|---|---|
| 1 | 0.82 | 5 | 20 | 2.5 |
| 2 | 0.82 | 7 | 20 | 1.5 |
| 3 | 0.82 | 10 | 20 | 1.0 |
| 4 | 0.82 | 5 | 30 | 2.5 |
| 5 | 0.82 | 7 | 30 | 2 |
| 6 | 0.82 | 8 | 30 | 2 |
| 7 | 0.82 | 10 | 30 | 1.5 |
| 8 | 0.67 | 6 | 20 | 1.5 |
| 9 | 0.67 | 10 | 20 | 1 |
| 10 | 0.67 | 5 | 30 | 2.5 |
| 11 | 0.67 | 6 | 30 | 2 |
| 12 | 0.67 | 7 | 30 | 2 |
| 13 | 0.67 | 10 | 30 | 1 |
| 14 | 0.54 | 4 | 30 | 2 |
| 15 | 0.54 | 6 | 30 | 1 |
| 16 | 1.0 | 5.6 | 20 | 5 |
| 17 | 1.0 | 6.7 | 20 | 5 |
| 18 | 1.0 | 9.4 | 20 | 4 |
| 19 | 1.0 | 4.2 | 30 | 5 |
| 20 | 1.0 | 6.2 | 30 | 5 |
| 21 | 1.0 | 8.4 | 30 | 4 |

Thus the examples indicate as an appropriate limit for the ratio of hydrogen peroxide:water at the start of the reaction, 0.8, which of course includes 0.82. As a lower limit that ratio can be 0.10; a preferred range is 0.30 to 0.60.

What is claimed is:

1. In the process of producing perpropionic acid by reaction of hydrogen peroxide and propionic acid in an aqueous medium and in the presence of sulfuric acid catalyst for the reaction, for production of an equilibrium mixture of perpropionic acid, propionic acid, hydrogen peroxide and water, and sulfuric acid catalyst, the improvement which comprises, for reduction of explosion hazard of the reaction mixture: employing a molar ratio of hydrogen peroxide: propionic acid of more than 3.5:1 and up to 10:1, a temperature of 20°–60° C, a weight ratio of hydrogen peroxide:water before the start of the reaction thereof with propionic acid, based on 100% hydrogen peroxide, of up to 0.8, the concentration of the sulfuric acid in the reaction mixture being 10–40% by weight.

2. Process of claim 1, wherein the temperature is 30°–45° C.

3. Process of claim 1 wherein said molar ratio of hydrogen peroxide:propionic acid is 3.8–10:1.

4. Process of claim 1, wherein said ratio of hydrogen peroxide:water is at least 0.10.

5. Process of claim 1, wherein said ratio of hydrogen peroxide:water is 0.30 to 0.60.

6. Process of claim 2, wherein said molar ratio of hydrogen peroxide-propionic acid is 3.8 – 10:1, and wherein said ratio of hydrogen peroxide:water is at least 0.10.

7. Process of claim 6, wherein said ratio of hydrogen peroxide:water is 0.30 to 0.60.

* * * * *

UNITED STATES PATENT AND TRADEMARK OFFICE
CERTIFICATE OF CORRECTION

PATENT NO. : 4,088,679
DATED : May 9, 1978
INVENTOR(S) : Günter Prescher et al

It is certified that error appears in the above-identified patent and that said Letters Patent are hereby corrected as shown below:

Column 1, line 18, "Bayer 2893" first occurrence should read -- Bayer 2892 --.

Signed and Sealed this

Seventeenth Day of October 1978

[SEAL]

Attest:

RUTH C. MASON
Attesting Officer

DONALD W. BANNER
Commissioner of Patents and Trademarks